United States Patent
Hansson et al.

(10) Patent No.: US 9,782,239 B2
(45) Date of Patent: Oct. 10, 2017

(54) FIXTURE, A THREAD MAKER AND A FIXTURE SET

(75) Inventors: Stig Hansson, Askim (SE); Anders Halldin, Mölndal (SE)

(73) Assignee: DENTSPLY International Inc, York, PA (US)

( * ) Notice: Subject to any disclaimer, the term of this patent is extended or adjusted under 35 U.S.C. 154(b) by 0 days.

(21) Appl. No.: 13/445,069

(22) Filed: Apr. 12, 2012

(65) Prior Publication Data

US 2012/0264085 A1    Oct. 18, 2012

Related U.S. Application Data

(60) Provisional application No. 61/475,331, filed on Apr. 14, 2011.

(30) Foreign Application Priority Data

Apr. 14, 2011  (EP) ..................................... 11162468

(51) Int. Cl.
    *A61C 8/00*    (2006.01)
(52) U.S. Cl.
    CPC .......... *A61C 8/0022* (2013.01); *A61C 8/0025* (2013.01); *A61C 8/0089* (2013.01)
(58) Field of Classification Search
    CPC ... A61C 8/0022; A61C 8/0025; A61C 8/0089; A61C 8/00
    USPC ............................... 433/172, 173–174, 201.1
    See application file for complete search history.

(56) References Cited

U.S. PATENT DOCUMENTS

| 5,823,777 A | 10/1998 | Misch et al. |
| 5,885,079 A * | 3/1999 | Niznick ............... A61C 8/0039 433/174 |
| 2004/0006346 A1* | 1/2004 | Holmen ............... A61C 8/0025 433/173 |
| 2006/0172258 A1* | 8/2006 | Niznick ............... A61C 8/0025 433/174 |
| 2008/0220394 A1* | 9/2008 | Berckmans ............ A61B 17/86 433/201.1 |

(Continued)

FOREIGN PATENT DOCUMENTS

| CN | 201775688 U | 3/2011 |
| EP | 0997112 A1 | 3/2000 |
| EP | 2233108 A1 | 9/2010 |

(Continued)

OTHER PUBLICATIONS

European Search Report, Application No. 11162468.0, Published Mar. 2, 2012.

(Continued)

*Primary Examiner* — Cris L Rodriguez
*Assistant Examiner* — Mirayda A Aponte
(74) *Attorney, Agent, or Firm* — David A. Zdurne; Douglas J. Hura; Leana Levin

(57) ABSTRACT

The invention relates to a fixture, such as a dental fixture, for insertion into a bore hole arranged in bone tissue. The fixture has two condensation portions, which may be designed to provide the same or different tensile strain levels to the cortical and cancellous bone tissue, respectively. The invention also relates to a thread maker for making a female thread in bone tissue prior to insertion of a fixture. The invention further relates to a fixture set, having a thread maker and a fixture.

30 Claims, 6 Drawing Sheets

(56) References Cited

U.S. PATENT DOCUMENTS

2009/0136898 A1  5/2009  Kim
2011/0070558 A1  3/2011  Park et al.

FOREIGN PATENT DOCUMENTS

| EP | 2292176 A1 | 3/2011 |
|---|---|---|
| WO | 0003657 A1 | 1/2000 |
| WO | 03015654 A1 | 2/2003 |
| WO | 2005079697 A1 | 9/2005 |
| WO | 2009054005 A2 | 4/2009 |
| WO | 2009054650 A1 | 4/2009 |
| WO | 2009072764 A1 | 6/2009 |

OTHER PUBLICATIONS

McCalden R. W. et al, Age-related changes in the tensile properties of cortical bone, The Journal of Bone and Joint Surgery, vol. 75-A No. 8, Aug. 1993.
Shunmugasmy V. C. et al, High strain rate response of rabbit femur bones, Journal of Biomechanics, 2010; 43: 3044-3050.
Gibson, J. Biomechanics, vol. 18, No. 5, pp. 317-328, 1985.
Kold, S. et al., Compacted cancellous bone has a spring-back effect. Acta Orthopaedica Scandinavica, 2003; 74 (5): 591-595.
International Search Report, Application No. PCT/EP2012/056725, Apr. 14, 2011.
Partial European Search Report, Application No. 11162468.0, Published date Sep. 27, 2011.

\* cited by examiner

FIXTURE, A THREAD MAKER AND A FIXTURE SET

TECHNICAL FIELD

The present invention relates to a fixture for insertion into a bore hole arranged in bone tissue, the fixture comprising threaded cutting and non-cutting portions. The invention also relates to a thread maker, and to a fixture set comprising a thread maker and a fixture.

BACKGROUND OF THE INVENTION

A frequent way today to restore a damaged limb, such as lost tooth, is to install a fixture in the adjacent bone tissue and replace the damaged parts. In this respect, for a successful result, the fixture should become fully stable and correctly joined to the bone. The term osseointegration is used for this joining effect, the basic meaning of this term being the bone tissue growth into the fixture surface. The two major contributors to this joint are a mechanical joint and an organic joint. The former being generally influenced by the macro geometry of the bore into which the fixture is installed, and by the macro geometry of the fixture, and is a direct effect of how well these two work together. The latter one being a continuously evolving and developing effect, particularly the time immediately after installation, and being generally influenced by how well the micro surface structure of the fixture interacts with the bone tissue.

Due to ingrowth there will be an interlocking effect between the bone and the fixture. Also, the mechanical joint is developed over time since the bone tissue, under ideal conditions, may grow into surface cavities of the fixture, and grow into voids left between the fixture and the bore after installation.

During installation of a fixture into the bone tissue, the bone is subjected to both stress and strain. The relationship between stress and strain is substantially linear up to a yield point (yield strain). Up to the yield point the bone is deformed elastically. However, beyond the yield point the bone will deform plastically. In order to provide for good healing conditions and stability of the fixture in the bone, care is taken to maintain the elasticity of the bone tissue and to avoid exceeding the yield point.

There is a continuous endeavour in the industry to further increase the stability of fixtures implanted in bone tissue and to improve the basic conditions during the healing phase after fixture installation. One example is the provision of the fixture surface with different types of structures, such as micro-roughened or blasted structures for increasing the contact surface between the fixture and the bone.

Nevertheless, there is till room for further development of fixtures as regards their stability in bone tissue.

SUMMARY OF THE INVENTION

An object of the present invention is to provide a fixture, in particular a dental fixture, which has a high stability/strength during the healing phase of the fixture. This and other objects, which will become apparent in the following, are accomplished by means of a fixture defined in the accompanying claims.

The present invention is based on the insight that applying a static strain to the bone tissue during and after implantation may be beneficial to the strength/stability of the fixture during the healing phase of the bone. Actually, the inventors have realized that even strains exceeding the yield point of the bone may be beneficial. In particular, the inventors have found that tensile strains in the circumferential direction which exceed the ultimate strain of the bone, i.e. when the bone cracks, may also be beneficial to trigger the biological response during the healing phase after fixture installation. Although cracks may be formed near the fixture, there will be present stabilizing surrounding bone tissue.

The inventors have further realized that the yield point and ultimate strain of cancellous bone is higher compared to the yield point and ultimate strain, respectively, of cortical bone. The inventors have also realized that a fixture may be designed to provide differentiated strain effect on bone tissue. Thus, the fixture may, for instance, be designed to provide a higher strain level at fixture portions intended to be in contact with cancellous bone tissue and a lower strain level at fixture portions intended to be in contact with cortical bone tissue.

According to a first aspect of the invention, a fixture for insertion into a bore hole arranged in bone tissue is provided. The fixture comprises:

a threaded first portion provided with at least one apical cutting edge for making a female thread in the bone tissue, a threaded non-cutting second portion located coronally of the first portion and being wider than the first portion with respect to major and/or minor fixture diameter, a threaded third portion located coronally of the second portion and provided with at least one coronal cutting edge for processing the female thread already made by the first portion and/or for making a separate female thread in the bone tissue, a threaded non-cutting fourth portion located coronally of the third portion and being wider than the third portion with respect to major and/or minor fixture diameter.

The insertion of a fixture with a certain torque means that static strains will be induced in the surrounding bone. The magnitude of these static strains do not only depend on the insertion torque but also depend on the fixture design, the shape of the bone preparation, the bone anatomy, the bone quality and possibly also on the fixture surface topography. Rather than to elaborate on these different parameters, some of which are difficult to estimate, the inventors have ingeniously realized that it is possible to achieve an adequately controlled static strain by fixture design.

In a circular geometry, the tensile strain in the circumferential direction is given by the increase in circumference divided by the initial circumference. For instance, with an initial diameter D the circumference is $\pi \cdot D$. If the diameter is increased by $\Delta D$, then the new circumference becomes $\pi \cdot (D + \Delta D)$. Thus, the increase in circumference is $\pi(D+\Delta D) - \pi \cdot D = \pi \cdot \Delta D$. Dividing the increase in circumference with the initial circumference of $\pi \cdot D$ results in a strain $\Delta D/D$.

By providing a female thread with a first radius r in the bone tissue surrounding the bore hole (the radius being the distance from the bore hole axis to the bone thread) and by providing the fixture with a threaded portion having threads at a second radius R which is larger than the first radius r, a pressure will be applied to the bone when said threaded portion is rotated into the bone via said bone threads. The enlarged radius R will thus lead to a condensation of the bone tissue. In analogy with the above explained strain $\Delta D/D$, the maximum strain will thus be $$\frac{R-r}{r}.$$

This means that by controlling the difference in radius between said threaded fixture portion and the bone thread with which the threads of said portion will mate, a controlled static strain may be achieved.

For instance, by having a threaded leading portion of the fixture with a first radius r corresponding to the radius of the bone threads, i.e. the distance from bore hole axis to the bone threads, and a threaded trailing portion having a second radius R which is larger than said first radius said controlled strain may be achieved.

In practice, the bone threads may be achieved either by pre-tapping with a separate tapper or by tapping means, such as cutting edges, on a self-tapping fixture as presented in the first aspect of the invention.

Thus, when installing the fixture according to the first aspect of the invention, the apical cutting edge of the first portion will make a female thread in the bone tissue, and as the fixture thread of the second portion (which lacks cutting edges) enters the female bone thread it will, because of its larger width, apply a radial pressure onto the bone tissue. When the fixture has been fully inserted into the bone, said second portion is submerged and no longer in contact with the marginal bone. Nevertheless, the radial pressure provided by the second portion at its submerged location in the bone will be maintained, and thus a static tensile strain will be provided to the bone tissue around said second portion.

Similarly, after the second portion has already entered the bone, the coronal cutting edge of the third portion will follow and will either process the female thread already made by the apical cutting edge or make a separate female thread in the bone tissue. In other words, the female thread already provided in the bone tissue may be further hollowed/deepened so that the major and/or minor female bone thread diameter is increased by the coronal cutting edge. As the fixture thread of the fourth portion (which lacks cutting edges) enters the deepened female bone thread it will, because of its larger width, apply a radial pressure onto the bone tissue.

By appropriately dimensioning the width of the second portion to the width of the female bone thread created by the apical cutting edge a suitable strain is achievable. Likewise, the width of the fourth portion should be suitably dimensioned in relation to the deepened female bone thread as processed by the coronal cutting edge, thereby achieving a suitable strain. In the alternative when the coronal cutting edge makes a separate female thread in the bone, the width of the fourth portion should be dimensioned in relation to that separate female thread.

Actually, the coronal cutting edge may be provided at a multiple thread, wherein one of the thread spirals is a continuation of the thread spiral interrupted by the apical cutting edge, while another thread spiral has its thread start in e.g. the third portion. In such case, the coronal cutting edge will both process the female bone thread created by the apical cutting edge (because of the common thread spiral) and create a separate female bone thread (because of the other thread spiral). The fixture threading (suitably also multiple-thread) in the fourth portions, may be appropriately dimensioned to provide a suitable strain.

Since the second and fourth portions are overdimensioned, in the sense that female bone threads in which the fixture thread of the second and fourth portions will pass has a smaller width than the width of said fixture thread, the second and fourth portions will act a condensation portions, i.e. they will at least locally condense/compress the surrounding bone tissue.

Thus, it should be understood that the static strain may either be provided by having an increased minor diameter of the second portion compared to the first portion (and/or fourth portion compared to the third portion) or by having an increased major diameter of the second portion compared to the first portion (and/or fourth portion compared to the third portion). Another alternative is an increase with regard to both major and minor diameter.

In other words, the radial distance from the fixture axis to a thread bottom may be larger in the second and fourth portions compared to the radial distance from the fixture axis to a thread bottom in the first and third portions, respectively. Alternatively, the radial distance from the fixture axis to a thread top may be larger in the second and fourth portions compared to the radial distance from the fixture axis to a thread top in the first and third portions, respectively. Thus, the minor diameter is generally determined by the thread bottoms or core of the fixture, while the major diameter is determined by the thread tops (or more specifically a geometrical circumferential surface which is tangential to the thread tops).

Suitably, for installation of a fixture according to the first aspect of the invention, the bore hole at the cortical bone may be widened, in order to avoid a too high strain which might otherwise be provided by the second portion on the cortical bone. This will allow a high strain to be applied to the cancellous bone, without providing the same high strain to the cortical bone during installation.

According to at least one example embodiment, the difference in major fixture diameter between the second portion and the first portion is greater than the difference in major fixture diameter between the fourth portion and the third portion. Similarly, according to at least one example embodiment, the difference in minor fixture diameter between the second portion and the first portion is greater than the difference in minor fixture diameter between the fourth portion and the third portion. Thus, because the diameter difference in these embodiments is greater at the apical strain-creating zone (comprising the first and second portions) than at the coronal strain-creating zone (comprising the third and fourth portions), a higher strain can be provided to the bone surrounding the apical strain-creating zone than to the bone surrounding the coronal strain-creating zone. The apical strain-creating zone may, suitably, be located at an area of the fixture intended to be in contact with cancellous bone tissue, which has comparatively high yield point and ultimate strain. The coronal strain-creating zone may, suitably, be located at an area of the fixture intended to be in contact with cortical bone tissue, which has comparatively low yield point and ultimate strain.

It should be understood that the general inventive idea is not limited to providing different strains to cancellous and cortical bone, but rather to provide the possibility to design a fixture which has two axially separated strain-creating zones, which may either provide the same level of strain or different levels of strain. For instance, both strain-creating zones may be designed to be present on areas of the fixture intended for cancellous bone.

According to at least one example embodiment, the fixture comprises an apical transition portion which tapers in the apical direction and which is arranged between said first portion and said second portion. According to at least one example embodiment, the fixture comprises a coronal transition portion which tapers in the apical direction and which is arranged between said third portion and said fourth portion.

The apical transition portion may be regarded as an intermediate portion having an apical end which borders to the first portion and a coronal end which borders to the second portion. The apical transition portion is provided for achieving the increased diameter, i.e. to widen the fixture from the first portion to the second portion. The transition portion may be threaded. However, alternatively, it may be non-threaded. The function of the transition portion can be regarded as to radially displace the thread tops and/or thread bottoms. It should be understood that any axial section of the fixture having larger width (such as larger major and/or minor diameter; or larger radial distance from fixture axis to thread top/bottom) than the largest fixture width at the apical cutting edge, is not part of the first portion but instead part of the transition portion or the other coronally located portions.

The coronal transition portion may have the corresponding characteristics as the apical transition portion discussed above, however, instead of being related to the first and second portions, the coronal transition portion is related to the third and fourth portions.

The first and third portions may be regarded as leading portions, while the second and fourth portions may be regarded as trailing portions. Thus, a transition portion may be provided to achieve a diametrical increase between a leading portion and a trailing portion along the apical-coronal direction of the fixture. According to at least one example embodiment, at least one of the leading portions is substantially cylindrical. According to at least one example embodiment, at least one of the leading portions is tapering. According to at least one example embodiment, a coronal part of at least one of the leading portions is cylindrical while an apical part thereof is tapering, or vice versa. Thus, at a transversal border plane where a leading portion and a transition portion meet, the extensions of the two portions may form an angle of less than 180°, regardless of the shape of the leading portion.

According to at least one example embodiment, the leading portion and the transition portion may both be tapered, wherein the angle formed between the two portions is 180°. In such case, the coronal end of the cutting edge(s) in the leading portion may be used to define the transversal border plane where the leading portion and the transition portion meet.

The second and/or fourth portions, i.e. the trailing portions, may suitably be cylindrical in order to provide a foreseeable static strain to the bone. However, alternatively, the second and/or fourth portions may be slightly widening in the coronal direction in order to compensate for any grinding effect caused by the threads rotating in the bone. In case of a coronally widened second portion and/or fourth portion, such a widening per axial unit length should not exceed the widening of the transition portion. Therefore, any widening of the second and/or fourth portions should, suitably only compensate for grinding effects and not to further increase the strain on the bone.

It should be understood that the apical and/or coronal transition portions do not necessarily have to be conically widened in the coronal direction (i.e. conically tapered in the apical direction), but can have other alternative shapes. For instance, according to at least one example embodiment, the coronal widening of the apical and/or coronal transition portions presents a concave or convex shape.

Also, the second and fourth portions may have alternative shapes. According to at least one example embodiment, at least one of the second and fourth portions is substantially cylindrical. According to at least one example embodiment, at least one of the second and fourth portions is tapering. According to at least one example embodiment, a coronal part of at least one of the second and fourth portions is cylindrical while an apical part thereof is tapering, or vice versa. According to at least one example embodiment, a coronal part of at least one of the second and fourth portions is tapering in the coronal direction to provide relief for the bone and allow it to flex back towards the fixture.

According to at least one example embodiment the third portion comprises a thread spiral which is continuous with a thread spiral of the second portion. Thus, contrary to for instance a zygomatic screw, such as the one illustrated in WO 2005/079697, which has a threadless middle section, the fixture according to the above embodiment has a thread spiral which interconnects the second and third portion. Thus, the second and third portions may be inserted into the same bone tissue. Indeed, according to at least one example embodiment, said first, second, third and fourth portions are each adapted to be anchored in a bone tissue surrounding a blind bore.

According to at least one example embodiment, the third portion comprises a thread spiral which upon insertion into the bore hole is received by the female thread made by the first portion. This will facilitate insertion of the fixture into the bone. Thus, the cutting edge in the third portion may further deepen the female thread already made by the cutting edge of the first portion, although in other embodiments the cutting edge of the third portion may cut a completely new female bone thread.

According to at least one example embodiment, each one of said first portion and said second portion is provided with at least one thread spiral, and each one of said third portion and said fourth portion is provided with at least one more thread spiral than said first and second portions and having the same lead as said at least one thread spiral in the first and second portions. This will provide both a good primary fixation and a good long-term fixation of the fixture in the bone. Having more thread spirals in the third and fourth portion enables the stiffness of the fixture to be increased, thereby improving the ability of the fixture to transmit loads more evenly to the bone tissue. If this is done at the cortical or marginal bone, the risk of marginal bone resorption is reduced.

According to at least one example embodiment, each one of said first, second and third portions is provided with at least one thread spiral, and said fourth portion is provided with at least one more thread spiral than said first, second and third portions and having the same lead as said at least one thread spiral in the first, second and third portions.

According to at least one example embodiment, the number of thread spirals in said fourth portion is a multiple integer of the number of thread spirals in said second portion.

In order to be able to provide a thread spiral in the fourth portion following the path of a thread spiral in the second portion, it is beneficial if the number of thread spirals in the fourth portion is a multiple integer of the number of thread spirals in the second portion. Hence, if there is provided one thread spiral in the second portion, the number of thread spirals in the fourth portion may be two, three, four and so on. If there is provided two thread spirals in the second portion, the number of thread spirals in the fourth portion may be four, six, and so on. If there is provided three thread spirals in the second portion, the number of thread spirals in the fourth portion may be six, nine, and so on.

According to at least one example embodiment, the smallest spacing between adjacent thread tops (peaks of the threading) in the fourth portion is smaller than the smallest spacing between adjacent thread tops (peaks of the threading) in the second portion.

When measuring the axial spacing between adjacent thread tops, the smallest spacing between adjacent thread tops in the fourth portion is smaller than the smallest spacing between adjacent thread tops in the second portion.

When measuring the axial spacing between adjacent thread tops, the measurement is to be taken between the radially outermost part of the threading and not in the valleys or flanks.

If the thread in the second portion has one thread spiral and the thread in the fourth portion has two thread spirals that are evenly distributed, the axial spacing between adjacent thread tops in the fourth portion will be approximately half the distance between adjacent thread tops in the second portion. If the thread in the second portion has one thread spiral and the thread in the fourth portion has three thread spirals that are evenly distributed, the axial spacing between adjacent thread tops in the fourth portion will be approximately a third of the distance between adjacent thread tops in the second portion.

However, there also exist fixtures in which the thread spirals are not evenly distributed. There also exist fixtures being provided with a major thread being provided with minor threads at its outer portion. In these cases, it is important to measure the distance between the major threads in one portion separately, and between the minor threads separately. Hence, one should not mix between the two different thread types in one portion of the fixture when measuring the smallest axial distance.

According to at least one example embodiment, the threads in the second portion have substantially the same thread profile as the profile of the threads in the first portion. According to at least one example embodiment, the threads in the fourth portion have substantially the same thread profile as the profile of the threads in the third portion.

Thus, in at least one example embodiment the thread profile along the threaded portions is constant throughout the entire fixture or throughout one of the previously mentioned apical strain-creating zone (first and second portions) and coronal strain-creating zone (third and fourth portions). According to an alternative example embodiment, the threads in the second and fourth portions have a larger thread profile compared to the profile of the threads in the first and third portions, respectively.

A thread profile comprises two flanks, a top interconnecting said two flanks, a bottom formed between two adjacent threads, said flanks forming an angle with a plane which is perpendicular to the fixture axis and which angle lies in a plane containing the extension of the fixture axis, said profile further having a height. Said top may comprise a top radius and said bottom may comprise a bottom radius.

According to at least one example embodiment, the threads in the second portion have substantially the same thread profile as the profile of the threads in the apical transition portion. According to at least one example embodiment, the threads in the fourth portion have substantially the same thread profile as the profile of the threads in the coronal transition portion.

According to at least one example embodiment, said thread profile is a microthread profile. According to at least one example embodiment, the threads in the second portion are microthreads having substantially the same profile as the outermost part of the threads in the apical transition portion. According to at least one example embodiment, the threads in the fourth portion are microthreads having substantially the same profile as the outermost part of the threads in the coronal transition portion.

By having a constant or substantially constant thread profile throughout the different portions in the respective strain-creating zones, the radial pressure caused by the second and fourth portions can be effectively controlled. In other words, with regard to the fixture axis, the thread profile may simply be subject to parallel displacement in the radial direction when comparing the first portion with the second portion (or comparing the third portion with the fourth portion).

According to at least one example embodiment, the threads in the first portion and the second portion have substantially the same top radius, the same apical flank angle and the same coronal flank angle. According to at least one example embodiment, the threads in the third portion and the fourth portion have substantially the same top radius, the same apical flank angle and the same coronal flank angle.

For instance, even though the threads in the third portion may at least partially be provided with macrothreads, while the fourth portion may be provided with microthreads, thus having different thread height, because of the same top radius and flank angles, the profile/contour of the microthreads will fit the profile/contour of the female bone threads created by the macrothreads. Thereby, the bone is well supported also by the microthreads. In such an example, suitably, part of the third portion may be provided with microthreads having a cutting edge for making female threads in the bone.

According to at least one example embodiment, the axial length of the threading of the second portion is greater than 1 mm, such as greater than 3 mm, suitably greater than 4 mm. Thus, the axial length of the threading of the second portion may be dimensioned to conform with at least a part of the thickness of the cancellous bone tissue.

According to at least one example embodiment, the axial length of the threading of the fourth portion is about 0.5-4 mm, suitably 1-3 mm. Such axial length substantially corresponds to normal thickness of cortical bone. Thus, fixtures according to such an embodiment are particularly suitable for applying a static strain to the cortical bone. Therefore, suitably, the fourth portion is a coronal end portion of the bone apposition surface of the fixture.

According to at least one example embodiment,
in said first portion the largest radial distance from the fixture axis to a thread top of said apical cutting edge is $r_t$,
in said second portion the smallest radial distance from the fixture axis to a thread top is $R_t$,
in said third portion the largest radial distance from the fixture axis to a thread top of said coronal cutting edge is $R'_t$,
in said fourth portion the smallest radial distance from the fixture axis to a thread top is $R''_t$,
wherein $r_t < R_t$, $r_t < R'_t$, and $R'_t < R''_t$.

Suitably, $R_t$ is equal to or smaller than $R'_t$. However, as long as the other relations in the just-mentioned embodiment are met, it is also conceivable to allow $R_t$ to be slightly larger than $R'_t$.

Accompanying FIG. 1 is an illustration of the relationship between stress and strain in the cortical bone tissue. The yield point is at the transition between the straight part (elastic deformation zone) and curved part (plastic deformation zone) of the graph. The ultimate strain is at the other end of the curved part.

Accompanying FIG. 2 is an illustration of the relationship between stress and strain in cancellous bone tissue. For cancellous bone, the behavior up to the yield point (i.e. where the straight part of the graph transits into the curved part) substantially corresponds to that in cortical bone. However, as may be seen from FIG. 2, the behavior above the yield point differs somewhat between cancellous bone and cortical bone.

It should be noted that the graphs in FIG. 1 and FIG. 2 illustrate the absolute values of the stresses and strains.

In this application, when strain is discussed, or when different values of strain are discussed, unless explicitly specified, the discussion may relate to tensile strain and/or compressive strain. All strain-related numbers are presented in absolute values.

The inventors have realized that a static strain in bone in the range of 0.01-0.3 (absolute values) provides a good bone strength during the healing phase, i.e. above the yield strain (for a normal 70 year old patient the yield strain of cortical bone may be below 0.01).

Thus, according to at least one example embodiment, the static strains provided by the fixture are in the range of 0.01-0.3.

Suitably, the strain created by the apical strain-creating zone (i.e. first and second portions of the fixture) is adapted to cancellous bone, and may advantageously be in the range of 0.06-0.3, suitably as in the range of 0.06-0.1. This is reflected in at least one example embodiment, according to which the ratio $$\frac{R_t - r_t}{r_t}$$

is in the range of 0.01-0.3, such as in the range of 0.06-0.3, suitably as in the range of 0.06-0.1.

Suitably, the strain created by the coronal strain-creating zone (i.e. third and fourth portions of the fixture) is adapted to cortical bone, and may advantageously be in the range of 0.01-0.1, such as in the range of 0.01-0.03, suitably in the range of 0.01-0.02. This is reflected in at least one example embodiment, according to which the ratio $$\frac{R''_t - R'_t}{R'_t}$$

is in the range of 0.01-0.1, such as in the range of 0.01-0.03, suitably in the range of 0.01-0.02.

The strain range of 0.01-0.02 is normally between the yield strain and ultimate strain of human cortical bone. However, as mentioned previously, even with strains exceeding the ultimate strain of human cortical bone, beneficial effects may be accomplished. Of course, for cancellous bone, considerably higher strains may be applied to the bone, since in cancellous bone the yield strain and ultimate strain are much higher than for cortical bone.

In analogy to the above discussed difference in width with respect to thread tops (major fixture diameter), the corresponding teaching may also be applied with respect to thread bottoms (minor fixture diameter).

Thus, according to at least one example embodiment
in said first portion the largest radial distance from the fixture axis to a thread bottom of said apical cutting edge is $r_b$,
in said second portion the smallest radial distance from the fixture axis to a thread bottom is $R_b$,
in said third portion the largest radial distance from the fixture axis to a thread bottom of said coronal cutting edge is $R'_b$,
in said fourth portion the smallest radial distance from the fixture axis to a thread bottom is $R''_b$,
wherein $r_b < R_b$, $r_b < R'_b$, and $R'_b < R''_b$.

Suitably, $R_b$ is equal to or smaller than $R'_b$. However, as long as the other relations in the just-mentioned embodiment are met, it is also conceivable to allow $R_b$ to be slightly larger than $R'_b$.

Similarly, according to at least one example embodiment, the ratio $$\frac{R_b - r_b}{r_b}$$

is in the range of 0.01-0.3, such as in the range of 0.06-0.3, suitably as in the range of 0.06-0.1, and/or the ratio $$\frac{R''_b - R'_b}{R'_b}$$

is in the range of 0.01-0.1, such as in the range of 0.01-0.03, suitably in the range of 0.01-0.02.

Thus, from the above discussion, it should now be clear that said strain levels may either be achieved by widening the fixture with respect to the major fixture diameter (the radial distance to the thread tops) or by widening the fixture with respect to the minor fixture diameter (the radial distance to the thread bottoms). Another alternative, is to widen the fixture both with respect to the major and minor fixture diameters. Also, it is conceivable to have different widening in the apical strain-creating zone and the coronal strain-creating zone. For instance, a fixture may comprise a second portion having, compared to a first portion, the same minor fixture diameter but larger major fixture diameter; and a fourth portion having, compared to a third portion, a larger minor fixture diameter but the same major fixture diameter. Other widening combinations are also conceivable.

The inventive fixture may be applicable to different parts of the human bone tissue. According to at least one example embodiment, said fixture is a dental fixture for arrangement in a jawbone.

According to at least one example embodiment the fixture is adapted for arrangement in the mandible such that each one of said first, second, third and fourth portions is anchored in the mandible. According to at least one example embodiment the fixture is adapted for arrangement in the maxilla such that each one of said first, second, third and fourth portions is anchored in the maxilla. Thus, according to these embodiments all four portions are anchored in a common bone tissue, unlike for instance a zygomatic implant which extends from the maxilla to the os zygomaticum.

According to a second aspect of the invention, there is provided a thread maker (tapper) adapted to be rotated into a bore hole arranged in bone tissue for making a female thread in the bone tissue prior to insertion of a fixture, the thread maker comprising
at least one apical cutting edge for making the female thread, and at least one coronal cutting edge for processing the bone thread already made by the apical cutting edge or for making a separate female thread in the bone tissue, the coronal cutting edge being axially spaced from the apical cutting edge.

Thus, if it is desired to use a fixture which is not self-tapping, a separate thread maker (tapper) may be used to make the female bone threads, and still enable strains to be provided to the bone tissue at axially separated levels in the bone (e.g. a certain strain value at the cancellous bone and different strain value at the cortical bone). The fixture which is to be inserted into the pre-tapped bore hole may be arranged without bone-condensing portions of different widths. The different strain levels are obtained by the design of the thread maker. Thus, although the fixture threading may be substantially constant in width along most of its axial length, the thread maker can create a shallower thread in the apical part of the bore hole and a deeper thread in the coronal part of the bore hole, thereby controlling the strain provided by said fixture to be higher in the bone forming the apical part of the bore hole than in the bone forming the coronal part of the bore hole. If the fixture threading has larger width at a coronal portion of the fixture then, with proper design of the coronal and apical cutting edges of the thread maker, the same value of strain could be achieved at two axially spaced apart locations in the bone.

An alternative is to have a fixture with varying width, e.g. such as the fixture discussed in connection with the first aspect of the invention, but without any cutting edges.

According to a third aspect of the invention, a fixture set is provided. The fixture set comprises a thread maker according to the second aspect of the invention in combination with a fixture. The fixture in said fixture set comprises an apical condensation portion for applying a radial pressure onto the female thread made by the apical cutting edge of the thread maker, and a coronal condensation portion for applying a radial pressure onto the section of the female thread processed or made by the coronal cutting edge of the thread maker.

The fixtures discussed in the various aspects and embodiments of the invention, may be dental fixtures. Such a dental fixture may be comprised in a dental implant. A dental implant may, in addition to the dental fixture, also comprise a superstructure, such as an abutment.

The dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

The dental fixture is a screw-type dental fixture. To this end the bore hole may be provided with internal (female) threads, in advance or may be left un-tapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A superstructure for connecting a prosthetic part to the fixture may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take. For instance, the prosthetic part may be secured directly to the dental fixture. A dental implant may thus comprise an abutment connected to the dental fixture, or the dental fixture without an abutment.

The term "coronal" is here and throughout this application used to indicate a direction towards a head end or trailing end of the dental implant. For instance, in a situation where an abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial distance" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the superstructure to the fixture. A rotational lock for the superstructure may be provided in the socket, such as an internal polygonal side wall, e.g. hexagonal, or alternatively one or more protrusions from or indentations in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

A conceivable alternative to having an abutment connected to the fixture is to have a one-piece implant, wherein a portion of the implant is embedded in bone tissue, while another portion of the implant extends from the bone tissue across the gingiva.

The fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

The length of the dental fixture may be in the range of 5-19 mm, depending on the clinical situation. The outer diameter of the dental fixture may suitably be in the range of 2-6 mm, such as 3-5 mm.

The fixture may be substantially cylindrical or slightly tapering from the coronal end towards the apical end. If the fixture has a slight tapering, the core of the fixture and the outer periphery defined by e.g. thread tops may have the same or different angle of taper. Furthermore, the core of the fixture may be cylindrical while the thread tops describe a conicity or, conversely, the core of the fixture may be tapered while the thread tops describe a generally cylindrical geometry. Alternatively, the fixture may comprise a combination of one or more cylindrical and/or one or more tapering portions. Thus, one or more portions of the fixture may have e.g. thread tops lying in a common imaginary cylindrical surface, which cylindrical surface is parallel with the longitudinal axis of the fixture. Alternatively or additionally, one or more portions of the fixture may have thread tops lying in an imaginary conical surface which in the apical direction is tapering towards the longitudinal axis.

The externally threaded fixture may comprise one or more thread spirals. Suitably, the fixture is threaded at least along 80% of its length, thereby providing an adequate anchoring in a bone tissue surrounding a bore hole, such as a blind bore hole.

The term "pitch" is used to indicate the axial distance between adjacent tops of a threading. The term "lead" is used to indicate the distance advanced parallel to the longitudinal axis when the fixture is turned one revolution, i.e. it corresponds to the pitch multiplied with the number of thread spirals. For a single thread spiral having a constant pitch, the lead is equal to the pitch; for a double thread spiral, the lead is twice the pitch.

The term "microthread" is used to indicate a thread having a height which is no greater than 0.2 mm. According to at least one example embodiment, the fixture is provided with microthreads having a height in the range of 0.02-0.2 mm, such as 0.05-0.015 mm, for instance 0.1 mm. The term "macrothread" is used to indicate a thread having a height which is greater than 0.2 mm. According to at least one example embodiment, the fixture is provided with macrothreads having a height in the range of 0.25-0.35 mm, such as 0.3 mm.

Suitably, microthreads may be located coronally of macrothreads. For instance, microthreads may be arranged to engage dense cortical bone and macrothreads may be arranged to engage porous spongious/cancellous bone. The lead of a microthread suitably corresponds to the lead of a macrothread. The macrothread pitch may, as an example, be 2-4 times, such as 3 times, the pitch of the microthreads. The pitch (top-to-top spacing) at a fixture portion provided with microthreads may be around 0.10-0.30 mm, for instance 0.20-0.24 mm. The pitch (top-to-top spacing) at a fixture portion provided with macrothreads may be around 0.30-0.90 mm, for instance 0.60-0.72 mm.

Microthreads can be regarded as defined, oriented roughness. A non-oriented roughness having smaller dimensions, for instance obtained by blasting, etching, etc., may be superimposed on microthreads as well as on macrothreads.

A thread profile may comprise two flanks, a top interconnecting said two flanks, a bottom formed between two adjacent threads, said flanks forming an acute angle v with a plane which is perpendicular to the fixture axis and which angle v lies in a plane containing the extension of the fixture axis, said profile further having a height D. The top may be curved and may have a top radius. Suitably, for $10° \leq v < 35°$, the top radius is greater than 0.4×D and, for $35° \leq v < 55°$, the top radius is greater than 0.2×D.

According to at least one exemplary embodiment, the flanks of the threads have a straight extension.

According to at least one exemplary embodiment, the flanks of the threads have a curved extension. It is for example conceivable with flanks having a concave curvature. It is also conceivable with flanks having a convex curvature.

DETAILED DESCRIPTION OF THE DRAWINGS

Figure 1:
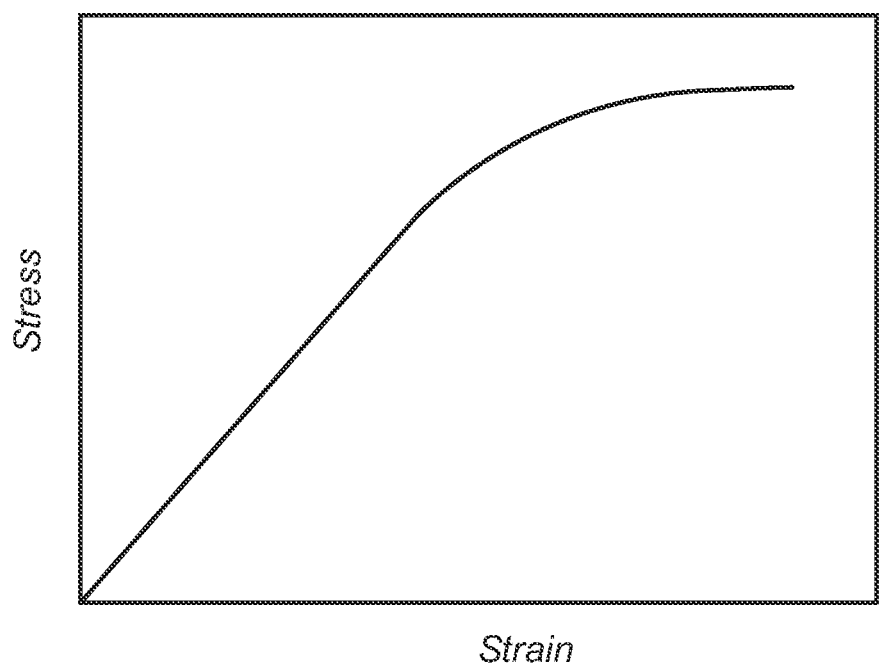
FIG. 1 is a graph illustrating a stress/strain relationship for cortical bone.

FIG. 1 is a graph illustrating a stress/strain relationship for cortical bone. In an article by McCalden R. W. et al. the relationship between ultimate strain and age is presented (McCalden R. W. et al., *Age-related changes in the tensile properties of cortical bone*, The Journal of Bone and Joint Surgery, Vol. 75-A. No. 8, August 1993). From the article, one learns that the ultimate strain is substantially linearly dependent on the person's age. For instance, an 80 year old person has in cortical bone an ultimate strain of about 0.015, a 50 year old person has an ultimate strain of about 0.025, while a 20 year old person has an ultimate strain of about 0.035. For cortical bone the yield strain is about half the ultimate strain. For instance, with reference to FIG. 1, in a 20 year old person, for a strain up to about 0.018, the stress/strain relationship could be linear and represents an elastic deformation of the bone. The interval between 0.018 and 0.035 is non-linear and represents a plastic deformation of the cortical bone. Similarly, for an 80 year old person, a strain up to 0.008 would correspond to the linear relationship and the interval between 0.008 and 0.015 would correspond to the non-linear relationship in FIG. 1.

EXAMPLE

Screw shaped fixtures, manufactured from commercially pure titanium, grade 4, were used. In order to reduce a possible grinding effect during insertion the fixtures had a turned surface. The endosseous part of the fixtures comprised three different portions; one leading (cutting) portion, one transition portion with a gradual increase in diameter and one trailing (condensation) portion. The bone bed was drilled to a final burr diameter of 3.3 mm corresponding to the core diameter ($2r_b$) of the cutting portion of the fixture. When the fixture was inserted the cutting features created a cavity in the bone which was congruent with the fixture shape of the cutting portion. When the transition portion entered the bone it created a gradual increase in the strains in the surrounding bone without cutting. When finally the condensation portion entered the bone the predetermined bone condensation was obtained. The fixtures were installed with a standardized rotation speed of 20 revolutions/minute. Two types of test fixtures were used; one where the increase in diameter was 0.15 mm (referred to as "Group 0.15") and another with a diameter increase of 0.05 mm (referred to as "Group 0.05"). The control fixtures had no diameter increase.

The fixtures were inserted in tibia of rabbits. Test fixtures were always inserted in the left leg and control fixtures in the right leg. Group 0.15 fixtures were installed proximally in the proximal tibia metaphysis. Group 0.05 fixtures were installed distally in, the proximal tibia metaphysis.

After 3.5 weeks, all fixtures were subjected to removal torque (RTQ) tests. The peak RTQ was investigated with a computerized control RTQ device, in which the values were transmitted at a frequency of 100 per second to the computer via a control box.

The fixture head was connected to the instrument, and an increasing reverse torque was applied to all the fixtures until failure of the bone-fixture interface occurred. The first peak values of resistance to reverse torque rotation were recorded in Ncm.

Prior to the animal experiment a 2D axisymmetric finite element model of the trailing portion of the fixture and the surrounding bone was developed. The fixture and the bone were modelled in a CAD software Pro/Engineer (PTC Corporate Needham, Mass. USA) and then transferred into the finite element software ANSYS 12.01 (ANSYS, Inc. Canonsburg, Pa., USA). The strain in the bone was induced by radial displacement of the fixture surface by 0.025 mm and 0.075 mm simulating a diameter increase of 0.05 mm and 0.15 mm respectively. The simulated maximum principal strain in the surrounding bone for Group 0.15 fixtures was ~0.045 (0.15 mm divided by 3.3 mm=0.045). For group 0.05 fixtures the maximum principal strain obtained was ~0.015 (0.05 mm divided by 3.3 mm=0.015).

In all sites the removal torque of the test fixtures was higher than that of the corresponding control fixtures. See Table 1.

TABLE 1

Comparison between removal torque for test fixtures and control fixtures.

| Removal | Average torque Test Ncm (Std) | Average torque Control Ncm (Std) |
|---|---|---|
| Tibia proximal (Group 0.15) | 26.0 (6.89) | 16.8 (7.83) |
| Tibia distal (Group 0.05) | 23.0 (5.31) | 17.2 (5.29) |

Strain in cortical bone from rabbits has been measured by Shunmugasamy V. C. et al. and presented in an article (Shunmugasamy V. C. et al., *High strain rate response of rabbit femur bones*. Journal of Biomechanics, 2010; 43: 3044-3050). The ultimate strain of rabbit cortical bone was measured to be about 0.02.

In the present study the fixtures were just supported by cortical bone. It should be noted that the Group 0.15 fixtures gave rise to strains (0.045) which exceeded the ultimate strain (~0.02) of cortical rabbit bone. In spite of this there was no evidence of reduced removal torque. On the contrary the removal torque of the experimental fixtures was higher than that of the control fixtures which were designed not to produce static strains in the bone. It is striking that the very highest removal torque was obtained for Group 0.15 fixtures for which the strains induced by far exceeded the ultimate strains. From the values in Table 1, one can simply calculate that for Group 0.15 fixtures the removal torque was increased by 55%, and for Group 0.05 fixtures the removal torque was increased by 34%. Obviously, the stresses in the bone, which were induced during fixture insertion, are maintained for a considerable time.

This study indicates that an increased strain provides better initial fixture stability, it is also noticeable that increased strain provides a better stability after 3.5 weeks.

In the above-mentioned article by McCalden R. W one learns that the ultimate strain is substantially linearly dependent on the person's age. The above discussed ultimate strain (~0.02 of rabbits) can be seen for a 70 year old person. While the rabbit experiments in the above discussed example showed a successful result for a strain of 0.045, which by far exceeds the ultimate strain of cortical rabbit bone (2¼ times the ultimate strain of cortical rabbit bone), and also exceeds the ultimate strain of cortical bone of a 70 year old human, it is anticipated that an even higher strain would be successful in a younger person's cortical bone. For a 20 year old person, it would correspond to applying a strain of about 0.08 (2¼ times the ultimate strain 0.035 of a 20 year old person). For a child or adolescent the ultimate strain is even higher, for instance 0.04, which means that a strain of 0.09 could be applied. The rabbit study in the above example did not measure the upper limit for suitable static radial strain, but since the Group 0.15 fixtures surprisingly provided an even better result than the 0.05 fixture, it is reasonable to assume that even higher strains relative to the ultimate strain may be suitable for cortical bone.

While the above study analyzed the strain in cortical bone, an analogy may be made to strains in cancellous bone. Thus, similarly to the previous explanations with regard to providing a tensile strain in cortical bone above the yield strain, a beneficial biological response may also be triggered by providing a tensile strain in cancellous bone above the yield strain of the cancellous bone.

Figure 2:
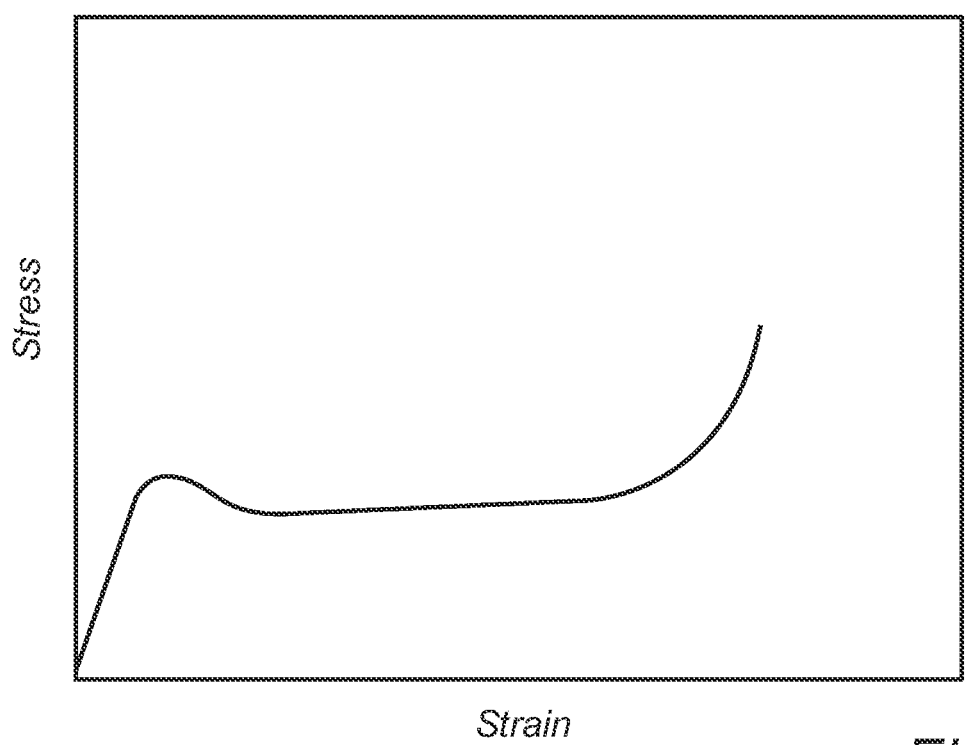
FIG. 2 is a graph illustrating a stress/strain relationship for cancellous bone.

FIG. 2 is a graph illustrating a stress/strain relationship for cancellous bone. The behavior of the graph up to the yield point is similar to that of FIG. 1, i.e. a linear relationship is presented. However, the curved part above the yield point is different and more stretched. According to Gibson, the yield strain is about 0.06 for cancellous bone (Gibson, J. Biomechanics, Vol. 18, No. 5, pp 317-328, 1985). Drawing conclusions from an article by Kold S. et al. (Kold S. et al., *Compacted cancellous bone has a spring-back effect*. Acta Orthopaedica Scandinavica, 2003; 74(5): 591-595) the yield strain for cancellous bone may be even higher. According to Kold S. et al. a bore hole of 5.0 mm in diameter was made in cancellous bone. The bone was then compacted by expanding the bore to 5.6 mm, after which the bone sprung back. During the compaction, the tensile strain ΔD/D on the cancellous bone was therefore 0.6/5=0.12. Thus, the yield strain in cancellous bone is multiple that of the yield strain in cortical bone. In addition, the plastic deformation of cancellous bone is much more stretched than for cortical bone. Thus, since a strain level of 0.1 is considered by the inventors to be suitable for cortical bone tissue, at least for some age groups, a strain level of 0.3 should be suitable for cancellous bone tissue.

Figure 3:
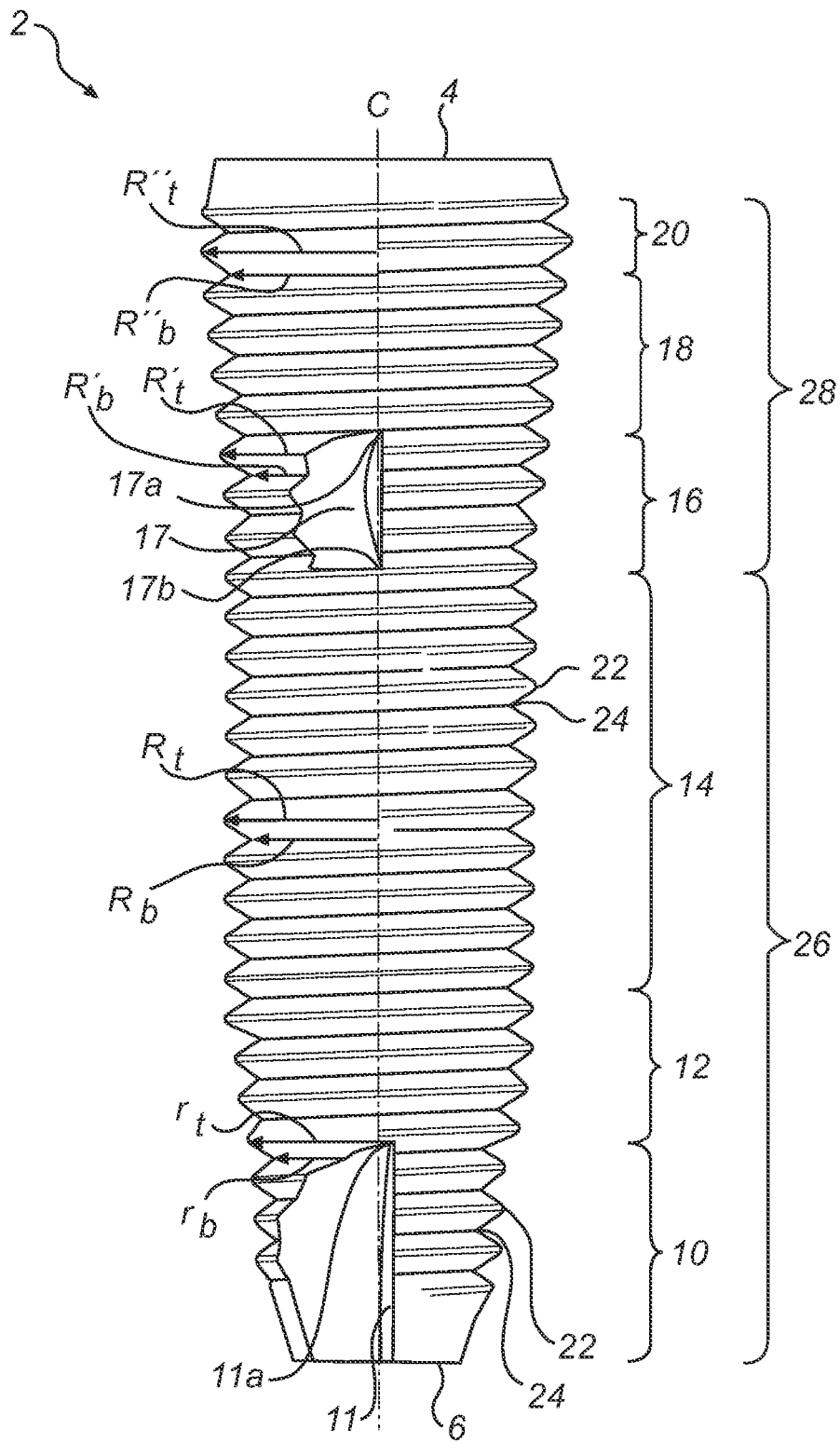
FIG. 3 illustrates a fixture according to at least one example embodiment of the invention.

FIG. 3 illustrates a fixture 2 according to at least one example embodiment of the invention. The fixture 2 comprises a coronal end 4 and an apical end 6. Extending coronally from the apical end 6 is a threaded first portion 10 provided with at least one apical cutting edge 11 for making a female thread in the bone. For instance there may be two, three, four or more cutting edges, suitably evenly distributed around the central axis of the fixture 2. The entire first portion 10 may be threaded or, as illustrated in FIG. 3, an apical section of the first portion 10 may be non threaded. The first portion 10 may be substantially cylindrical or, as illustrated in FIG. 3, tapering towards the apical end 6. Another alternative is to have a substantially cylindrical coronal section of the first portion 10 and a tapering apical section. For the purpose of providing the desired strain to the bone tissue, it does not matter which of the shapes the first portion 10 has. Instead, with respect to dimensioning the strain, what matters is the width of the first portion 10 at the coronal end 11a of the apical cutting edge 11. This width is what will determine the depth of the female thread created in the bone. A threaded non-cutting second portion 14 of the fixture 2 which is overdimensioned in relation to the depth of the female thread will create the strain in the bone.

An apical transition portion 12 is located between the first portion 10 and the second portion 14. Thus, the apical transition portion 12 borders apically to the first threaded portion 10 and coronally to the second threaded portion 14. The apical transition portion 12 lacks cutting edges and widens the fixture 2 in the coronal direction. The second portion 14 is substantially cylindrical and will therefore, when arranged in the female bone thread which has been cut by the apical cutting edge 11, provide a substantially static tensile strain to the surrounding bone tissue. The second portion could be made slightly widening in the coronal direction in order to compensate for any grinding effect.

In the illustrated embodiment, both the minor fixture diameter and major fixture diameter have increased from the first threaded portion 10 to the second non-cutting threaded portion 14. In other words, $$\frac{R_t - r_t}{r_t} > 0,$$

$$\frac{R_b - r_b}{r_b} > 0,$$

wherein, $r_t$ is the largest radial distance from the central fixture axis C to a thread top 22 of said apical cutting edge 11 in said first portion 10, $R_t$ is the radial distance from the central fixture axis C to a thread top 22 in said second portion 14, $r_b$ is the largest radial distance from the central fixture axis C to a thread bottom 24 of said apical cutting edge 11 in said first portion 10, $R_b$ is the radial distance from the central fixture axis C to a thread bottom 24 in said second portion 14.

Suitably, the above ratios may be in the range of 0.01-0.3, such as in the range of 0.06-0.3, suitably as in the range of 0.06-0.1.

Thus, the above ratios provide a measure of the tensile strain which may be provided to the bone by the apical strain-creating zone 26 (which comprises the first portion 10 and the second portion 14 and the intermediate apical transition portion 12). Within the apical strain-creating zone 26, the first portion 10 may be regarded as a leading portion, while the second portion 14 may be regarded as a trailing or condensation portion. The apical strain-creating zone 26 is suitably configured and dimensioned to affect cancellous bone tissue.

The fixture 2 is also provided with a coronal strain-creating zone 28, which comprises a threaded third portion 16, a coronal non-cutting transition portion 18 and a threaded non-cutting fourth portion 20. Within the coronal strain-creating zone 28, the third portion 16 may be regarded as a leading portion and the fourth portion 20 may be regarded as a trailing or condensation portion. The coronal strain-creating zone 28 is suitably configured and dimensioned to affect cortical bone tissue.

More specifically, in the illustration of FIG. 3, the third portion 16 having at least one coronal cutting edge 17 borders to the second portion 14. Thus, the third portion 16 can be regarded as starting with the apical end 17b of said coronal cutting edge 17 and terminating with the coronal end 17a of said coronal cutting edge 17.

Unless the bore in the bone has been prepared so as to have a greater diameter at the coronal cortical bone compared to the apical cancellous bone, then the second portion 14 will provide the above discussed strain also to the cortical bone during insertion of the fixture 2. However, as the coronal cutting edges 17 of the third portion 16 follows the second portion 14 during insertion of the fixture 2, the strain in the bone will at least temporarily be relieved since the female bone threads will be cut deeper by the third portion 16 rather than being condensed by the second portion 14.

Similarly to the apical strain-creating zone 26, the thread profile of the coronal strain-creating zone 28 remains unchanged and both the minor and major fixture diameters are increased from the third portion 16, via the coronal non-cutting transition portion 18, to the fourth non-cutting portion 20. In other words, $$\frac{R''_t - R'_t}{R'_t} > 0,$$

$$\frac{R''_b - R'_b}{R'_b} > 0,$$

wherein, $R'_t$ is the largest radial distance from the central fixture axis C to a thread top 22 of said coronal cutting edge 17 in said third portion 16, $R''_t$ is the radial distance from the central fixture axis C to a thread top 22 in said fourth portion 20, $R'_b$ is the largest radial distance from the central fixture axis C to a thread bottom 24 of said coronal cutting edge 17 in said third portion 16, $R''_b$ is the radial distance from the central fixture axis C to a thread bottom 24 in said fourth portion 20.

Suitably, the above ratios may be in the range of 0.01-0.1, such as in the range of 0.01-0.03, suitably in the range of 0.01-0.02.

Figure 4:
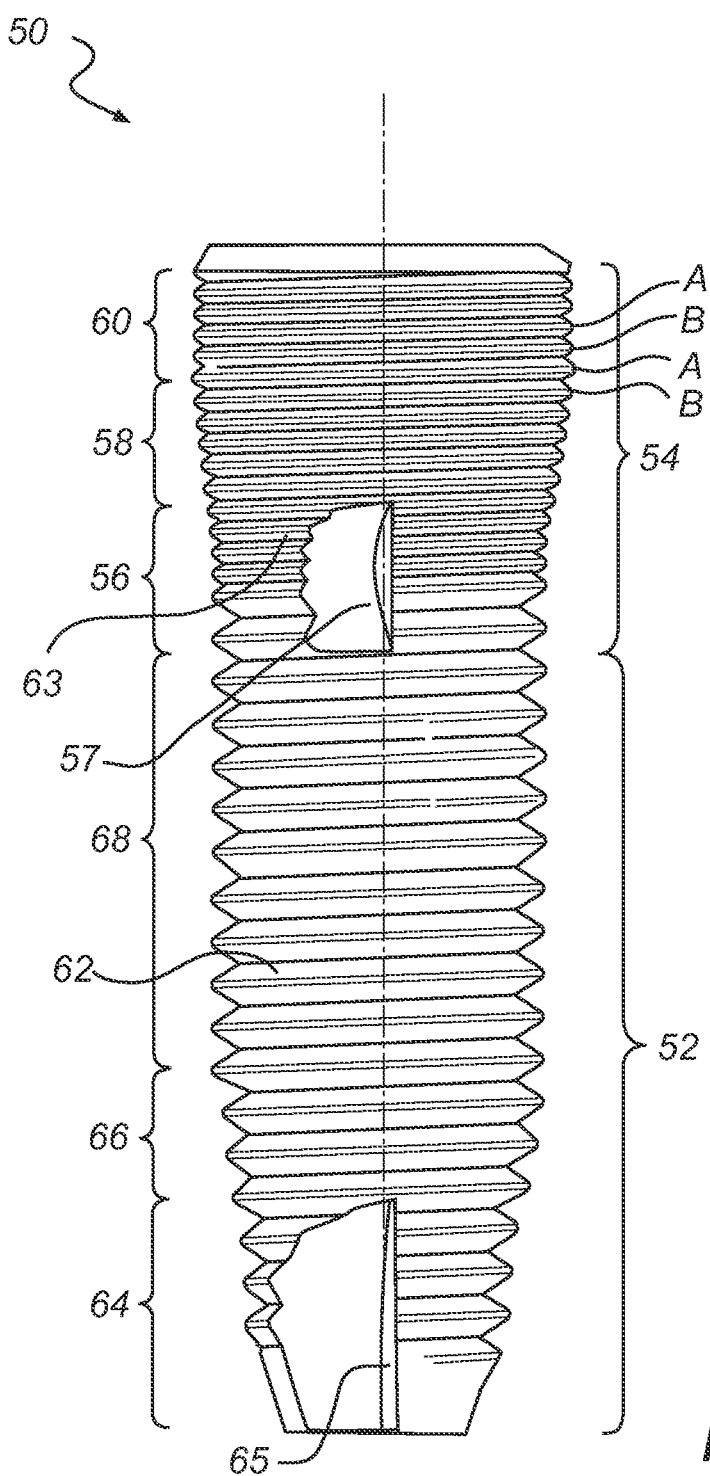
FIG. 4 illustrates a fixture according to at least another example embodiment of the invention.

FIG. 4 illustrates a fixture 50 according to at least another example embodiment of the invention. The apical strain-creating zone 52 of the fixture 50 in FIG. 4 corresponds to the apical strain-creating zone 26 of the fixture 2 in FIG. 3. However, the coronal strain-creating zone 54 of the fixture 50 in FIG. 4 is different from the coronal strain-creating zone 28 of the fixture 2 in FIG. 3.

The coronal strain-creating zone 54 of the fixture 50 shown in FIG. 4 has a third threaded portion 56 provided with at least one cutting edge 57, which is coronally followed by a fixture-widening coronal transition portion 58, which in turn is coronally followed by a threaded non-cutting fourth portion 60. About halfway along the axial extension of the third portion 56, the threading is changed. The single thread spiral 62 which runs from the first portion 64, via the apical transition portion 66 and the second portion 68, to the third portion 56 changes into a double thread spiral 63 having the same lead as the single thread spiral 62, but half the pitch of the single thread spiral 62. The smaller axial top-to-top distance of the double thread spiral 63 enables the stiffness of the fixture 50 to be increased, thereby improving the ability of the fixture 50 to transmit loads more evenly to the cortical bone tissue, which reduces the risk of marginal bone resorption.

Furthermore, the thread depth of the double spiral 63 is smaller than the thread depth of the single spiral 62. For instance, the large single thread spiral 62 may be a macrothread, while the smaller double thread spiral 63 may comprise microthreads. Nevertheless, the radius of curvature of the thread top and the angle of the thread flanks may be substantially the same for both types of threading. An example of profiles will be discussed later in connection with FIGS. 5a and 5b.

Continuing with FIG. 4, the coronal cutting edge 57 will thus cut two female thread spirals in the bone, one of which is new and one of which is a processing/deepening of the female bone thread already created by the apical cutting edge 65.

The following widening caused by the coronal transition portion 58 and the static strain provided by the fourth non-cutting portion 60 follows the previously discussed principles. Thus, the width of the fourth portion 60 compared to the width of the third portion 56 at the coronal cutting edge 57 will provide a measure of the tensile strain transmittable to bone tissue. It should be understood that since the third portion 56 and fourth portion 60 has a double thread spiral, which for explanatory purposes will now be referred to as spirals A and B, different strain-effects may be created. The strain caused by spiral A depends on the difference in width of spiral A in the third and fourth portions 56, 60. The strain caused by spiral B depends on the difference in width of spiral B in the third and fourth portions 56, 60. Thus, if as illustrated in FIG. 4, said differences between the third and fourth portions 56, 60 are the same for spiral A and spiral B, there will be no differentiation in strain between the two spirals. However, if, when comparing the fourth portion 60 with the third portion 56, spiral A has a larger increase in width than spiral B, then spiral A will provide a larger strain to the bone.

For the fixture 50 shown in FIG. 4, the strain levels provided to the bone by the apical strain-creating zone 52 and the coronal strain-creating zone 54 may suitably be in line with the levels discussed in connection with the fixture 2 of FIG. 3. However, other levels may also be achieved depending on how the different zones are configured.

Figure 5:
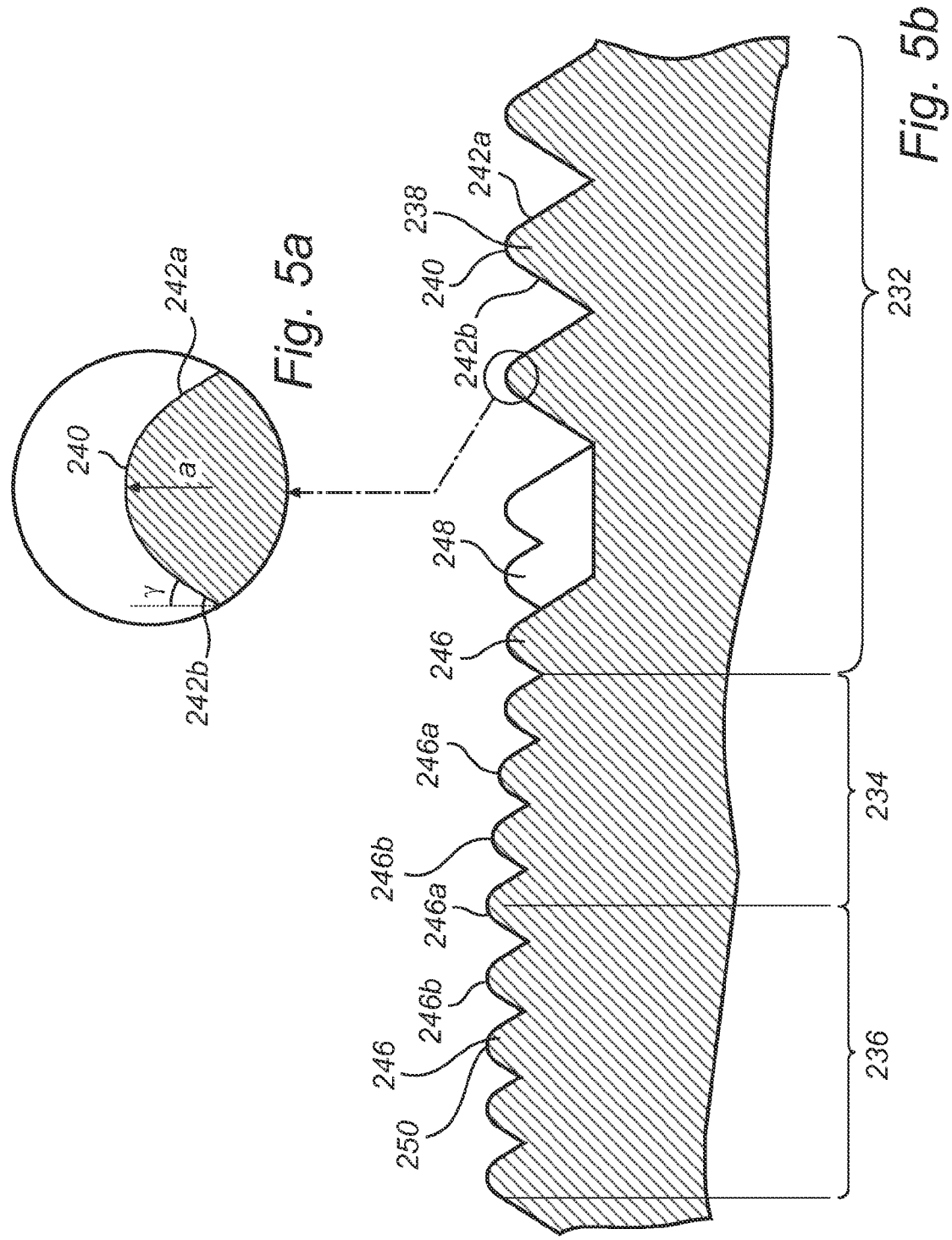
FIG 5a illustrates in cross-section a detail of a fixture according to at least one example embodiment of the invention.
FIG. 5b illustrates in cross-section a detail of a fixture according to at least one example embodiment of the invention.

FIGS. 5a-5b illustrate in cross-section a detail of a fixture according to at least one example embodiment of the invention. It may, for instance, be a detail of a coronal strain-creating zone, similar to the one shown in FIG. 4. Alternatively, it could be a detail of an apical strain-creating zone.

The fixture has a leading portion 232 (e.g. a third threaded portion as previously discussed), a coronally widening transition portion 234 and a substantially straight trailing portion 236 (e.g. a fourth threaded portion as previously discussed). The leading portion 232 is provided with macrothreads 238 having thread tops 240 with a certain radius of curvature a. The thread tops 240 are flanked by apical and coronal flank portions 242a, 242b at a certain acute angle γ relative to a plane perpendicular to the central fixture axis. The angle γ lies in the plane containing the fixture axis. In this case the apical and coronal flanks 242a, 242b are illustrated as having the same angle γ. However, in alternative embodiments the coronal and apical flank angles may differ from each other.

Coronally of the macrothreads 238, the leading portion 232 is also provided with double-spiraled microthreads 246 which continue into the transition portion 234 and the trailing portion 236. The microthreads 246 have the same lead as the macrothread 238, the pitch being half the pitch of the macrothread 238. A cutting feature 248 (e.g. the coronal cutting edge as previously discussed) is present at the microthreads in the leading portion 232 to make corresponding female microthreads in the bone tissue. In the illustrated embodiment, throughout the leading portion 232, transition portion 234 and trailing portion 236, the tops 250 of the microthreads 246 have the same radius of curvature as the radius of curvature a of the macrothreads 238. Also, the flank angles of the microthreads 246 correspond to those of the macrothreads 238. The effect of this conformation to the macrothreads 238 will now be explained.

The microthreads 246 are provided as two thread spirals, herein referred to as a first thread spiral 246a and a second thread spiral 246b. The first thread spiral 246a will follow the path of the macrothreads 238. The second thread spiral 246b will make its own path. Thus, when the first thread spiral 246a of the microthreads 246 enters the female bone thread it can theoretically be in full contact with the bone, since the thread tops have the same radius of curvature a and the flanks have the same angles γ as the female bone thread. This means that the initial stability of the fixture can be higher than if the first thread spiral of the microthreads would not fill out the space of the female bone thread. It should be noted that while the cutting features 248 at the microthreads 246 will make a new path for the second thread spiral 246b, it will just adapt the inner areas of the already made female bone thread to conform with the inner areas of the first thread spiral 246a.

Figure 6:
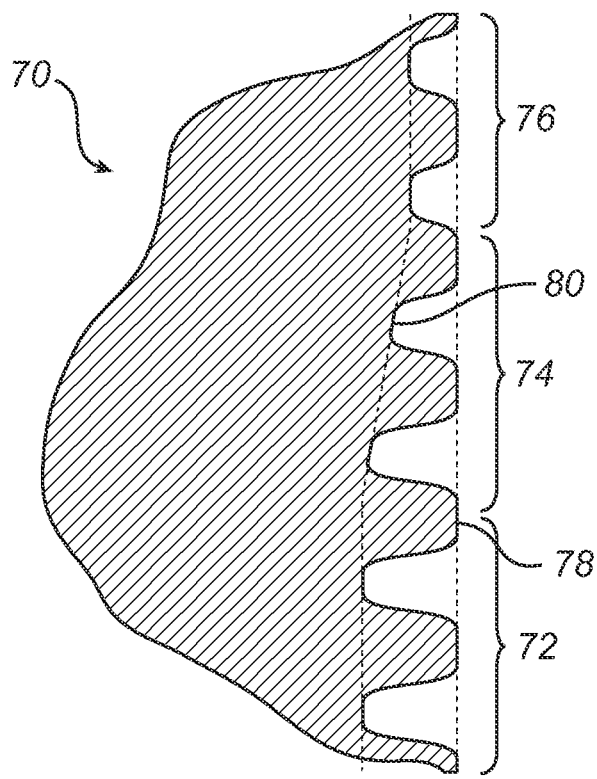
FIG. 6 illustrates in cross-section a detail of a fixture according to at least another example embodiment of the invention.

FIG. 6 illustrates in cross-section a detail of a fixture 70 according to at least one example embodiment of the invention. In this example, going from a leading portion 72 (i.e. first or third threaded portion), via a transition portion 74, to a trailing portion 76 (i.e. second or fourth non-cutting threaded portion), the radial distance from the fixture axis to the thread tops 78 is constant. Thus, the major fixture diameter remains unchanged. However, the outer surface formed by the thread bottoms 80 (i.e. minor fixture diameter) is changing throughout the different portions. Thus, the outer surface of the transition portion 74 formed by the thread bottoms 80 is conically widened away from that of the leading portion 72. In terms of the previously discussed radial distances (here taking the second and first portions as examples of trailing and leading portions, respectively), $R_t = r_t$, while $R_b > r_b$ wherein $$\frac{R_b - r_b}{r_b}$$

is in the range of 0.01-0.3. Thus, only the thread bottoms 80 provide said radial pressure to cause the desired static strain on the bone tissue.

Figure 7:
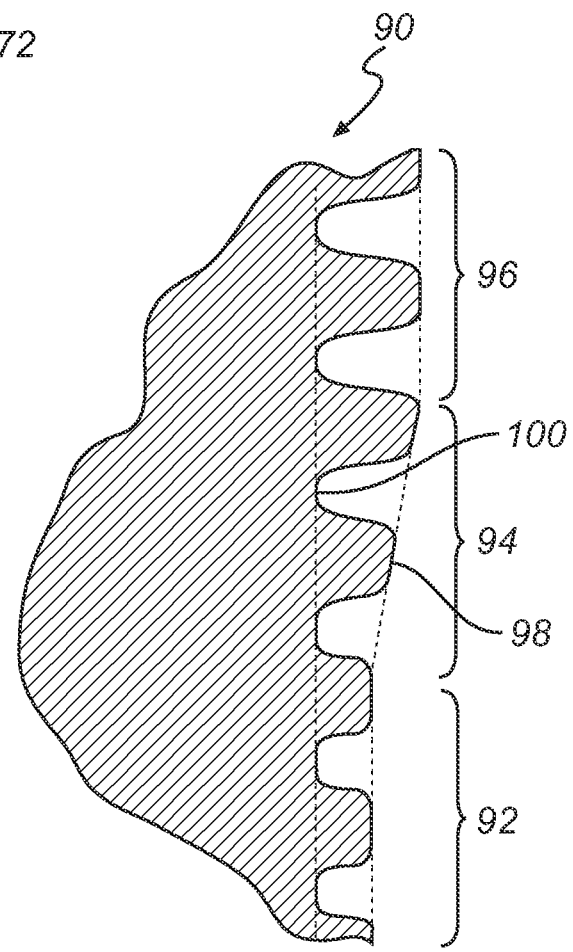
FIG. 7 illustrates in cross-section a detail of a fixture according to at least yet another example embodiment of the invention.

FIG. 7 illustrates in cross-section a detail of a fixture 90 according to at least one other example embodiment of the invention. In this example, going from the leading portion 92, via the transition portion 94, to the trailing portion 96, the radial distance from the fixture axis to the thread bottoms 100 is constant. However, the outer surface formed by the thread tops 98 is changing throughout the different portions. Thus, the outer surface of the transition portion 94 formed by the thread tops 98 is conically widened away from that of the leading portion 92. In terms of the previously discussed radial distances (again taking the second and first portions as examples of trailing and leading protions, respectively), $R_b=r_b$, while $R_t>r_t$, wherein $$\frac{R_t - r_t}{r_t}$$

is in the range of 0.01-0.3. Thus, only the thread tops 98 provide said radial pressure to cause the desired static strain on the bone tissue.

Thus, from FIGS. 6 and 7 it should be understood that it is within the scope of the inventive idea to provide a fixture having on the one hand an apical strain-creating zone in which the major and/or minor fixture diameter is widened coronally and on the other hand a coronal strain-creating zone in which the major and/or minor fixture diameter is widened coronally. Thus, it should be understood that the zones do not have to be widened in the same way. For instance, the apical strain-creating zone may have a widening major fixture diameter and a minor fixture diameter which is constant coronally of the apical cutting edge, while the coronal strain-creating zone may have a widening minor fixture diameter and a major fixture diameter which is constant coronally of the coronal cutting edge.

Figure 8:
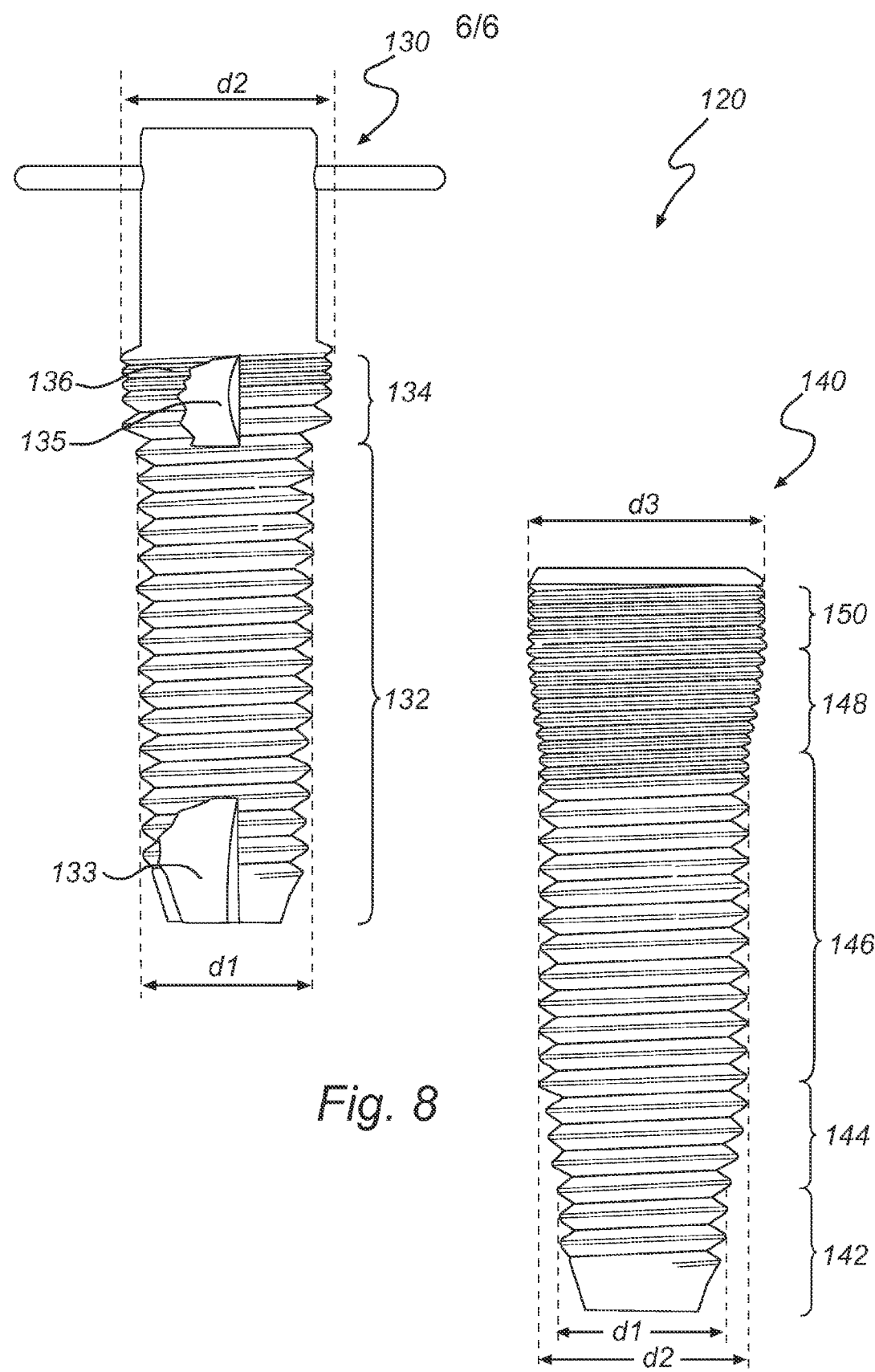
FIG. 8 illustrates a fixture set according to at least one example embodiment of the invention, the fixture set comprising a fixture and a thread maker according to at least one example embodiment of the invention.

FIG. 8 illustrates a fixture set 120 according to at least one example embodiment of the invention, the fixture set 120 comprising a fixture 140 and a thread maker 130 according to at least one example embodiment of the invention.

The tread maker 130 or tapper is adapted to be rotated into a bore hole arranged in bone tissue for making a female thread in the bone tissue prior to insertion of the fixture. The thread maker comprises an apical portion 132 and a coronal portion 134. The apical portion is provided with at least one apical cutting edge 133 for making a female thread in the bone having a major diameter d1. The coronal portion 134 being provided with a multiple thread spiral 136 is also provided with at least one coronal cutting edge 135 for making female threads having a major diameter d2. The multiple thread spiral 136 at the coronal portion 134 is in FIG. 8 exemplified as comprising microthreads, however, a single macrothread would be a conceivable alternative.

Thus, in the apical part of the bore hole, where cancellous bone is normally present, the female bone thread will have a smaller major diameter d1 compared to the diameter d2 in the coronal part of the bore hole, where cortical bone is normally present.

The fixture 140 to be inserted into the pre-threaded bore hole, comprises an apical leading portion 142, the major diameter of which is d1, i.e. corresponding to the major diameter of female bone thread in the apical part of the bore hole (the minor diameters also correspond to each other). Thus, the apical leading portion 142 will not exert a radial pressure onto the bone. Bordering coronally to the apical leading portion 142 is an apical transition portion 144 which widens the fixture 140 and will thus apply a pressure to the bone which is gradually increasing until it is leveled out by an apical trailing or condensation portion 146. The apical condensation portion 146 may suitably have said major diameter d2 and will thus provide a static tensile strain to the bone which at the apical parts of the bore hole has only been provided with a female thread of diameter d1.

Because the coronal portion 134 of the thread maker 130 will in the bore hole provide a female thread of diameter d2, i.e. the same as the diameter of the apical condensation portion 146 of the fixture 140, the apical condensation portion 146 will not exert any pressure to the cortical part of the bone when the fixture 140 is inserted, but only to the cancellous part.

Bordering coronally to the apical condensation portion 146 is a coronal transition portion 148 which further widens the fixture to a coronal trailing or condensation portion 150 having a major fixture diameter d3. As the coronal condensation portion 150 enters the coronal part of the bore hole having the female thread with diameter d2, it will because of the larger diameter d3, provide a tensile strain to the cortical bone tissue.

Thus, by appropriately choosing diameters d1, d2 and d3, desired strain levels for the cancellous and cortical bone, respectively, may be accomplished.

The invention claimed is:

1. A fixture for insertion into a bore hole arranged in bone tissue, comprising
a threaded first portion provided with at least one apical cutting edge for making a female thread in the bone tissue,
a threaded non-cutting second portion located coronally of the first portion and being wider than the first portion with respect to major and/or minor fixture diameter,
a threaded third portion located coronally of the second portion and provided with at least one coronal cutting edge for processing the female thread already made by the first portion and for making a separate female thread in the bone tissue, the threaded third portion having a cylindrical profile,
a threaded non-cutting fourth portion located coronally of the third portion, the threaded non-cutting portion having a cylindrical profile and being wider than the third portion with respect to major and/or minor fixture diameter;
a coronal widening transition portion coronally bordering the threaded third portion and apically bordering the threaded non-cutting forth portion;
wherein the threaded third portion includes a thread change such that a single thread spiral, which runs from at least the threaded non-cutting second portion into the threaded third portion, changes into at least a double thread spiral about the at least one coronal cutting edge of the threaded third portion.

2. The fixture as in claim 1, wherein the third portion comprises a thread spiral which upon insertion into the bore hole is received by the female thread made by the first portion.

3. The fixture as in claim 1, wherein said first, second, third and fourth portions are each adapted to be anchored in a bone tissue surrounding a blind bore.

4. The fixture as in claim 1, wherein the fixture is threaded at least along 80% of its axial length.

5. The fixture as in claim 1, wherein the difference in major fixture diameter between the second portion and the first portion is greater than the difference in major fixture diameter between the fourth portion and the third portion.

6. The fixture as in claim 1, wherein the difference in minor fixture diameter between the second portion and the first portion is greater than the difference in minor fixture diameter between the fourth portion and the third portion.

7. The fixture as in claim 1, comprising an apical transition portion which tapers in the apical direction and which is arranged between said first portion and said second portion, a coronal transition portion which tapers in the apical direction and which is arranged between said third portion and said fourth portion, or both.

8. The fixture as in claim 7, wherein the threads in the second portion have the same thread profile as the profile of the threads in the apical transition portion, the threads in the fourth portion have the same thread profile as the profile of the threads in the coronal transition portion, or both.

9. The fixture as in claim 1, wherein each one of said first portion and said second portion is provided with at least one thread spiral, and wherein each one of said third portion and said fourth portion is provided with at least one more thread spiral than said first and second portions and having the same lead as said at least one thread spiral in the first and second portions.

10. The fixture as claimed in claim 9, wherein the number of thread spirals in said fourth portion is a multiple integer of the number of thread spirals in said second portion.

11. The fixture as in claim 1, wherein the smallest spacing between adjacent thread tops in the fourth portion is smaller than the smallest spacing between adjacent thread tops in the second portion.

12. The fixture as in claim 1, wherein the threads in the second portion have the same thread profile as the profile of the threads in the first portion, the threads in the fourth portion have the same thread profile as the profile of the threads in the third portion, or both.

13. The fixture as in claim 12, wherein said thread profile is a microthread profile.

14. The fixture as in claim 1, wherein the threads in the first portion and the second portion have the same top radius, the same apical flank angle and the same coronal flank angle, the threads in the third portion and the fourth portion have the same top radius, the same apical flank angle and the same coronal flank angle, or both.

15. The fixture as in claim 1, wherein the axial length of the threading of the second portion is greater than 1 mm, the axial length of the threading of the fourth portion is about 0.5-4 mm, or both.

16. The fixture as in claim 1, wherein the axial length of the threading of the second portion is greater than 3 mm, the axial length of the threading of the fourth portion is about 0.5-4 mm, or both.

17. The fixture as in claim 1, wherein the axial length of the threading of the second portion is greater than 4 mm, the axial length of the threading of the fourth portion is about 13 mm, or both.

18. The fixture as in claim 1, wherein in said first portion, the largest radial distance from the fixture axis to a thread top of said apical cutting edge is $r_t$, in said second portion the smallest radial distance from the fixture axis to a thread top is $R_t$, in said third portion the largest radial distance from the fixture axis to a thread top of said coronal cutting edge is $R'_t$, in said fourth portion the smallest radial distance from the fixture axis to a thread top is $R''_t$, and wherein $r_t<R_t$, $r_t<R'_t$, and $R'_t<R''_t$.

19. The fixture as in claim 18, wherein the ratio $$\frac{R_t - r_t}{r_t}$$

is in the range of 0.01-0.3, wherein the ratio $$\frac{R''_t - R'_t}{R'_t}$$

is in the range of 0.01-0.1, or both.

20. The fixture as in claim 18, wherein the ratio $$\frac{R_t - r_t}{r_t}$$

is in the range of 0.06-0.3, wherein the ratio $$\frac{R''_t - R'_t}{R'_t}$$

is in the range of 0.01-0.03, or both.

21. The fixture as in claim 18, wherein the ratio $$\frac{R_t - r_t}{r_t}$$

is in the range of 0.06-0.1, wherein the ratio $$\frac{R''_t - R'_t}{R'_t}$$

is in the range of 0.01-0.02.

22. The fixture as in claim 1, wherein in said first portion the largest radial distance from the fixture axis to a thread bottom of said apical cutting edge is $r_b$, in said second portion the smallest radial distance from the fixture axis to a thread bottom is $R_b$, in said third portion the largest radial distance from the fixture axis to a thread bottom of said coronal cutting edge is $R'_b$, in said fourth portion the smallest radial distance from the fixture axis to a thread bottom is $R''_b$, and wherein $r_b<R_b$, $r_b<R'_b$, and $R'_b<R''_b$.

23. The fixture as claimed in claim 22, wherein the ratio $$\frac{R_b - r_b}{r_b}$$

is in the range of 0.01-0.3, wherein the ratio $$\frac{R''_b - R'_b}{R'_b}$$

is in the range of 0.01-0.1, or both.

24. The fixture as claimed in claim 22, wherein the ratio $$\frac{R_b - r_b}{r_b}$$

is in the range of 0.06-0.3, wherein the ratio $$\frac{R_b'' - R_b'}{R_b'}$$

is in the range of 0.01-0.03, or both.

25. The fixture as claimed in claim 22, wherein the ratio $$\frac{R_b - r_b}{r_b}$$

is in the range of 0.06-0.1, wherein the ratio $$\frac{R_b'' - R_b'}{R_b'}$$

is in the range of 0.01-0.02, or both.

26. The fixture as in claim 1, wherein said fixture is a dental fixture for arrangement in a jawbone.

27. The fixture as claimed in claim 26, wherein the fixture is adapted for arrangement in the mandible such that each one of said first, second, third and fourth portions is anchored in the mandible.

28. The fixture as claimed in claim 26, wherein the fixture is adapted for arrangement in the maxilla such that each one of said first, second, third and fourth portions is anchored in the maxilla.

29. The fixture as in claim 26, wherein the length of the fixture is 5-19 mm.

30. The fixture as in claim 1, comprising an apical transition portion which tapers in the apical direction and which is arranged between said first portion and said second portion and a coronal transition portion which tapers in the apical direction and which is arranged between said third portion and said fourth portion.

* * * * *